US008246944B2

(12) United States Patent
Cardona Iglesias et al.

(10) Patent No.: US 8,246,944 B2
(45) Date of Patent: Aug. 21, 2012

(54) IMMUNOTHERAPEUTIC AGENT FOR THE COMBINED TREATMENT OF TUBERCULOSIS IN ASSOCIATION WITH OTHER DRUGS

(75) Inventors: Pere Joan Cardona Iglesias, Mataró (ES); Isabel Amat Riera, Barcelona (ES)

(73) Assignee: Archivel Farma, S.L., Mataro (Barcelona) (ES)

( * ) Notice: Subject to any disclaimer, the term of this patent is extended or adjusted under 35 U.S.C. 154(b) by 449 days.

(21) Appl. No.: 10/577,840

(22) PCT Filed: Oct. 29, 2004

(86) PCT No.: PCT/ES2004/000482
§ 371 (c)(1),
(2), (4) Date: Feb. 1, 2007

(87) PCT Pub. No.: WO2005/042013
PCT Pub. Date: May 12, 2005

(65) Prior Publication Data
US 2007/0269501 A1    Nov. 22, 2007

(30) Foreign Application Priority Data

Oct. 31, 2003   (ES) .................................. 200302551

(51) Int. Cl.
*A01N 63/00* (2006.01)
*C12N 1/12* (2006.01)
(52) U.S. Cl. .................... 424/93.1; 435/243; 435/252.1; 435/253.1
(58) Field of Classification Search .......................... None
See application file for complete search history.

(56) References Cited

U.S. PATENT DOCUMENTS

| | | | | |
|---|---|---|---|---|
| 4,724,144 | A | | 2/1988 | Rook et al. |
| 4,744,984 | A | * | 5/1988 | Ragland ...................... 424/282.1 |
| 5,785,975 | A | * | 7/1998 | Parikh ......................... 424/278.1 |
| 6,001,361 | A | | 12/1999 | Tan et al. |
| 6,443,898 | B1 | * | 9/2002 | Unger et al. .................. 600/458 |
| 7,214,651 | B2 | * | 5/2007 | Mohr et al. .................... 510/161 |
| 2002/0094336 | A1 | * | 7/2002 | Andersen et al. .......... 424/190.1 |
| 2002/0127700 | A1 | | 9/2002 | Zhang |
| 2003/0165525 | A1 | * | 9/2003 | Andersen et al. .......... 424/190.1 |
| 2007/0269501 | A1 | | 11/2007 | Cardona Iglesias et al. |

FOREIGN PATENT DOCUMENTS

| | | |
|---|---|---|
| RU | 2 153 354 C1 | 7/2000 |
| WO | WO 00/21983 | 4/2000 |
| WO | WO 03/004520 A2 | 1/2003 |
| WO | WO 03/018053 A1 | 3/2003 |
| WO | WO 03/063897 A1 | 8/2003 |

OTHER PUBLICATIONS

Chatuverdi et al. Vaccine 17:2882-2887; 1999.*
Kumazawa et al. Japan J Microbiol 1976;20:183-190.*
Dhiman et al. Indian J Exp Biol 1999; 37:1157-66.*
Lyons et al. Infect Immunity 2002; 70:5471-8.*
Cummings et al. Hybridoma 1998; 17:151-6.*
Ribi et al. Annals NY Acad Sci 1976;277: 228-38.*
Sinha et al., Proteome analysis of the plasma membrane of *Mycobacterium tuberculosis*, Comparative and Functional Genomics, 2002, vol. 3, pp. 470-483.
International Search Report for International PCT Application No. PCT/ES2004/000482 mailed Mar. 3, 2005.
Anne L. Sørensen et al., "Purification and Characterization of a Low-Molecular-Mass T-Cell Antigen Secreted by *Mycobacterium tuberculois*," *Infection and Immunity*, May 1995, Vo. 63., No. 5., pp. 1710-1717.
V.A. Kabanov, "From synthetic polyelectrolytes to polymer-subunit vaccines", *Vysokomolekulamye soedinenia. Seria A I seria B*., ISSN 1023-3091, 2004, vol. 46., No. 5, abstract.
Orme, "Preclinical testing of new vaccines for tuberculosis: A comprehensive review", Science Direct, Vaccine vol. 24 (2006) 2-19.
Larson et al., "Immunology—Resistance to Tuberculosis in Mice immunized with BCG disrupted in Oil", Immunology, Nature Publishing Group, vol. 198, Jun. 22, 1963, pp. 1214-1215.
Chugh et al., "Protective Efficacy of Different Cell-Wall Fractions of *Mycobacterium tuberculosis*", Folia Microbiol. 37 (6), 407-412 (1992).
D.B. Pal and Shriniwas, "Role of cellwall vaccine in prophylaxis of tuberculosis", Indian J Med Res 65, 3, Mar. 1977, pp. 340-345.
Agger et al., "Specific Acquired Resistance in Mice Immunized with Killed Mycobacteria", Scand. J. Immunol. 56, 443-447, 2002.
Kaufmann, "Envisioning future strategies for vaccination against tuberculosis", Nature Reviews Immunology/AOP, published online Aug. 18, 2006.
Viniti Chaturvedi et al., "Protective antigens of *Mycobacterium habana* are distributed between peripheral and integral compartments of plasma membrane: a study in experimental tuberculosis of mouse," Vaccine, vol. 17, 1999, pp. 2882-2887.
Andre L. Moreira et al., Mycobacterial Antigens Exacerbate Disease Manifestations in *Mycobacterium tuberculosis*-Infected Mice, Infection and Immunity, Apr. 2002, p. 2100-2107, vol. 70, No. 4.
Joanne Turner et al., Effective Preexposure Tuberculosis Vaccines Fail to Protect When They Are Given in an Immunotherapeutic Mode, Infection and Immunity, Mar. 2000, p. 1706-1709, vol. 68, No, Douglas B. Lowrie et al. Therapy of Tuberculosis in Mice by DNA Vaccination, Nature, Jul. 15, 1999, p. 269-271, vol. 400.
Jennifer L. Taylor et al., Pulmonary Necrosis Resulting From DNA Vaccination Against Tuberculosis, Infection and Immunity, Apr. 2003, p. 2192-2198, vol. 71., No. 4.

\* cited by examiner 3.

*Primary Examiner* — Q. Janice Li
(74) *Attorney, Agent, or Firm* — RatnerPrestia

(57) ABSTRACT

This invention refers to an immunotherapeutic agent based on cell wall fragments from virulent *Mycobacterium tuberculosis* strains, to a method for obtaining this immunotherapeutic agent, to pharmaceutical formulations containing it and to its use for the preparation of a drug for the combined treatment of tuberculosis in association with other drugs.

28 Claims, No Drawings

IMMUNOTHERAPEUTIC AGENT FOR THE COMBINED TREATMENT OF TUBERCULOSIS IN ASSOCIATION WITH OTHER DRUGS

This application is a U.S. National Phase Application of PCT International Application No. PCT/ES2004/000482, filed Oct. 29, 2004.

FIELD OF INVENTION

This invention refers to a method for preparing a useful immunotherapeutic agent for the combined treatment of tuberculosis in association with other drugs. It is based on cell wall fragments of a virulent *Mycobacterium tuberculosis*-complex strain, and on the immunotherapeutic agent obtained with the aforementioned method.

BACKGROUND OF THE INVENTION

Tuberculosis is a chronic infectious disease caused by the *Mycobacterium tuberculosis*-complex (MTB-C) bacilli, which currently includes the following species: *M. tuberculosis, M. bovis, M. microti* and *M. africanum.*

According to the World Health Organization (WHO), there are 8,000,000 new cases of tuberculosis and some 3,000,000 people die every year. It is believed that there are 2,000,000,000 people infected worldwide.

The current vaccine used as a preventive treatment against tuberculosis is based on bacteria from the so-called BCG strain (Calmette-Guerin bacillus), a variety of *M. bovis.*

On the one hand, according to the WO-A-03018053, this is the best vaccine currently available to induce immunoprotection against tuberculosis. However, the safety and the effectiveness of this vaccine in humans remain controversial in some countries because it does not completely protect adults against pulmonary tuberculosis.

On the other hand, WO-A-03004520 describes as a known fact that the most effective treatment to fight tuberculosis in infected people, both for those who have and those who have not developed the disease, consists in the administration of several drugs, including isoniazid, for a period of several months.

This prolonged treatment may induce the development of microorganisms resistant to these drugs when the treatment is not completed and, moreover, the aforementioned drugs only act when the bacillus has an active metabolism (i.e., when it is growing) but not when it has a non-active metabolism. This is a significant inconvenience because during tuberculosis infection bacilli coexist in both an active and a non-active metabolism phase.

One possibility to solve these problems, as described in the patent U.S. Pat. No. 4,724,144, consists in the use of an immunotherapeutic agent based on dead *M. vaccae* cells as an adjuvant for the treatment to tuberculosis together with the administration of other drugs, such as rifampicin and isoniazid.

However, patent U.S. Pat. No. 6,001,361 states that such an adjuvant agent has not been used in large-scale vaccination of people against tuberculosis, and there is little information on its effectiveness.

Therefore, an immunotherapeutic agent is needed for the treatment of tuberculosis to act as a coadjuvant for these drugs, and this agent must not induce the development of resistant microorganisms and also generate immunologic response even against bacilli in a non-active phase.

The authors of this invention have discovered a method that allows the preparation of a new immunotherapeutic agent useful for the combined treatment of tuberculosis in association with other drugs. This immunotherapeutic agent contains cell wall fragments of a virulent MTB-C strain that may increase the effectiveness of the associated drugs to generate an effective immunologic response against bacilli that are not in an active metabolism, thus also reducing the risk of resistance.

The object of this invention is to provide a method to obtain an immunotherapeutic agent containing cell wall fragments of a virulent MTB-C strain, useful for the combined treatment of tuberculosis in association with other drugs.

The immunotherapeutic agent obtained using the previous method and the use of this agent for preparing a drug for the combined treatment of tuberculosis in association with other drugs are also included in the object of this invention.

Moreover, another additional object consists in the pharmaceutical compounds made with this immunotherapeutic agent.

DETAILED DESCRIPTION OF THE INVENTION

The invention provides a method to obtain an immunotherapeutic agent containing cell wall fragments of a virulent MTB-C strain, which is useful for the combined treatment of tuberculosis in association with other drugs.

The invention further provides an immunotherapeutic agent and pharmaceutical compounds obtained using this method and the use of these compounds for treating a person with tuberculosis.

The method to obtain an immunotherapeutic agent that contains cell wall fragments from a virulent *Mycobacterium tuberculosis*-complex (MTB-C) strain is characterized in that it includes the following steps:

Culture of the virulent MTB-C strain for a period of time of three weeks or longer, and Homogenization of the cell culture in a non-ionic tensioactive compound.

The virulent strain may be any virulent strain of MTB-C, since the tuberculosis bacillus is very stable and no mutations have been described in immunogenic compounds. One of the strains most frequently used by the researchers in this field, and considered as the strain of reference, is the so-called H37Rv strain that for example may be freely obtained from the National Collection of Type Cultures (NCTC), London, Great Britain (deposit number NC007416).

The virulent strain may be cultured by inoculation in culture media well known by a person skilled in the art. It may be a solid media, such as Middlebrook 7H10 or 7H11-type agar, or a liquid media, such as the Sauton or the Proskauer-Beck culture media.

As regards this invention, the culture must be maintained for a period of time of three weeks or longer, preferably between 3 and 4 weeks. The temperature of the culture is preferably maintained at between 34° C. and 38° C.

Following the completion of the culture, if it has been conducted in a solid phase, the plates are scraped to obtain the colonies while avoiding media extraction (agar). If the culture has been conducted in a liquid phase, the cells are concentrated and washed using conventional techniques known by a person skilled in the art (e.g., centrifugation).

The homogenization of the strains is carried out in a buffered media at a neutral pH. In this invention, it is important that the homogenization is conducted in the presence of a non-ionic tensioactive compound that favors the obtaining of finely divided cell wall particles and at least partial emulsions of unwanted lipidic fractions.

By means of this homogenization method, MTB-C cells break and small fragments of cell wall are obtained.

The homogenization may be carried out using sonication by ultrasounds, or small beads with a diameter of approximately 1 mm (e.g., of silica or silica-zirconium) together with a mechanical homogenizer. A mechanical homogenizer such as the BEADBEATER model of the company Biospec may be used.

The buffered media is made up, for example, with PBS buffer (saline solution of phosphate buffer).

The type of non-ionic tensioactive compound used is not crucial, although it is preferable to choose one from the alkylphenol ethoxylate group and the ethoxylated sorbitan esters. It is better that the non-ionic tensioactive compound is selected from the octylphenol ethoxylate compounds. Most preferably, octylphenol ethoxylate with 7-8 mol of ethylene oxide are used; these may be found in the market under the name TRITON X-114, for example. The concentration of the non-ionic tensioactive compounds during homogenization ranges between 1 and 5% of the total weight homogenized.

The homogenized mass containing the desired cell wall fragments, undergoes a conventional treatment in order to separate these fragments both from non-fragmented cells and the solubilized compounds.

For example, after separating the silica or silica-zirconium (if used) by decantation, the homogenized product is gently centrifuged at a speed slower than 5,000 rpm in order to remove the non-fragmented cells as sediments.

Then, the resulting supernatant is centrifuged at a higher speed (for example, higher than 15,000 rpm) to remove the solubilized elements that concentrate in the supernatant liquid, whereas the cell wall fragments concentrate in the sediment. Using conventional techniques known by a person skilled in the art, such as washing in PBS buffer and centrifugation, this method may be repeated several times until a completely clear supernatant is obtained; this is then rejected.

The sediment obtained that contains cell wall fragments is dispersed in PBS buffer and undergoes a chemical (e.g., treatment with formol) or physical (e.g., treatment in autoclave or pasteurization) method to guarantee the total inactivation of the MTB-C cells that could have been viable after fragmentation and purification.

Finally, the dispersion of cell wall fragments in PBS buffer is distributed into vials and is lyophilized at a temperature of between −15° C. and −25° C. and a vacuum of between 0.1 and 0.5 mbar.

Vials with cell wall fragments of MTB-C are thus obtained that form the immunotherapeutic agent of this invention, and are kept at −70° C.

From the immunotherapeutic agent of the invention, several pharmaceutical compounds may be prepared, and this is also one of the objects of the invention; these may be formulated as an oil-type emulsion in water (O/W) or as liposomes. Liposome-type pharmaceutical compositions are preferred.

The formation of liposomes may be carried out using conventional techniques, well known by a person skilled in the art. For example, liposomes may be obtained mixing the lyophilized cell wall fragments and the adjunct lipids in an aqueous medium to form liposomes, and homogenizing the mixture using a standard method, such as a high speed shaker.

The adjunct lipids to form liposomes are widely known by a person skilled in the art. In general, they include phospholipids with a net neutral and/or negative charge and sterols.

The phospholipids used may be, for example: phosphatidylcholine, phosphatidylserine and phosphatidylinositol.

Normally the most abundant component in liposomes is phosphatidylcholine, which may be synthesized or isolated from natural sources. A frequently used marketed product is soybean lecithin.

The sterols used in the preparation of liposomes may be, among others, cholesterol and bile salts.

Preferably, liposomes are formed using a mixture of soybean lecithin and sodium cholate.

Optionally, liposomes may have additives to improve their stability, such as vitamin E, which acts as a lipid antioxidant.

The liposomes obtained vary in size, and 99.9% are smaller than 1 micron.

Liposomes may undergo lyophilization to obtain the immunotherapeutic agent that is the object of the invention as lyophilized liposomes.

The object of the invention also includes the use of the immunotherapeutic agent to prepare a drug for the combined treatment of tuberculosis in association with other drugs.

Preferably, but not excluding other routes of administration, the immunotherapeutic agent that is the object of the invention is administered by parenteral route.

Among the known antituberculosis drugs, the ones that are preferred for the combined treatment with the therapeutic agent of this invention are isoniazid and rifampicin.

The association between the immunotherapeutic agent of the invention and the antituberculosis drugs for the combined treatment of this disease may be carried out simultaneously or sequentially, e.g., by the simultaneous administration of the drugs and the immunotherapeutic agent, or by the previous administration of drugs followed by the administration of the immunotherapeutic agent.

Surprisingly, it has been found that the combined treatment of tuberculosis by the administration of the immunotherapeutic agent of the invention associated with drugs for the treatment of tuberculosis increases the efficacy of these drugs because it generates an immunologic response against bacilli than are not in an active metabolic phase, thus also reducing the risk of developing resistances.

The following examples provide a person skilled in the art with a detailed description of specific embodiments within the invention.

EXAMPLE 1

Obtaining the Immunotherapeutic Agent

Some 80-100 plates of Middlebrook 7H11-type agar are inoculated with H37Rv culture provided by the National Collection of Type Cultures (NCTC), London, Great Britain (deposit number NC007416). The concentration of the colony-forming units inoculated in each plate is $10^5$-$10^6$UFC. The plates are incubated for 21 days (3 weeks) at a temperature of between 34° C. and 38° C.

After incubation, the colonies are removed from the agar plates using a spatula, and being careful in order to not remove the culture medium. Between 15 and 18 g of crude extract are obtained.

The crude extract is dispersed in approximately 20 mL of PBS buffer that contains 4% weight of TRITON X-114. 35 mL of silica-zirconium beads with 1 mm of diameter are added, and then mechanic homogenization is carried out using a BEADBEATER homogenizer manufactured by Biospec.

The homogenization method is continued until less than 5 whole bacilli are detected after observation of 100 fields at 1000 augments following staining with the Ziehl-Neelsen technique.

The product resulting from the homogenization is separated from the silica-zirconium beads by decantation. These are washed in a PBS-buffered solution with 4% weight of TRITON X-114, and the liquid from the different washes are collected with the product, thus obtaining a total volume of about 80-100 mL.

Then the product resulting from the homogenization plus the liquid from washing is centrifuged at 3,000 rpm for 30 minutes in a refrigerated centrifuger at 40° C., so as to remove non-fragmented cells from the sediment.

The supernatant is kept.

Then, the supernatant is centrifuged at 15,100 rpm (equivalent to 27,000 g) for 60 minutes at 4° C., thus obtaining a whitish sediment that contains the cell wall fragments.

The sediment is kept, and the yellowish supernatant is discarded.

The sediment is first washed in PBS buffer (3×3 mL) and then redispersed in 3 mL of the buffer solution, brought to 20 mL with PBS buffer and then centrifuged again at 15,100 rpm for 60 minutes at 4° C.

The supernatant obtained is discarded.

Washing and centrifugation are repeated until the supernatant obtained is completely clear. After each centrifugation the supernatant is discarded.

The sediment containing the cell wall fragments is washed in PBS buffer (3×3 mL) and redispersed in 12 mL of PBS buffer.

After the centrifugation and the wash, all the volume resulting from the dispersion of cell wall fragments in PBS buffer is collected in a container and is pasteurized by treatment at 65° C. for 1 hour.

Then, the mixture is rapidly cooled down in an ice bath, and the cell wall fragment dispersion is distributed into cryotubes at a rate of 1 mL per cryotube.

The cryotubes with the dispersed cell wall fragments are frozen at −70° C. and lyophilized at a temperature of between −15° C. and −22° C. and a vacuum between 0.180 and 0.400 mbar.

Between 1 and 1.5 g of immunotherapeutic agent are obtained.

EXAMPLE 2

Obtaining Liposomes of the Immunotherapeutic Agent

Between 740 and 770 mg of the product obtained in example 1 are weighed in a beaker. Then, 20 mL of a dispersion of pharmacy-quality soybean lecithin in ethanol (1 kg of lecithin in 1 liter of absolute ethanol) and 7 mL of a solution of pharmacy-quality sodium cholate in water (200 g of sodium cholate in 1 liter of bidistilled water) are added.

The pH is adjusted to a value between 7.7 and 8 with a solution of HCl 0.997 N.

Liposomes are prepared by homogenization using a high-speed shaker.

The liposome dispersion obtained this way is diluted to 10% in bidistilled water; the pH is adjusted to a value of between 7.1 and 7.3 with a solution of HCl 0.0997 N.

The liposome dispersion is distributed into cryotubes (0.5 mL per tube) and is frozen at −80° C.

Next, they are lyophilized and the immunotherapeutic agent (the object of the invention) is obtained as liposomes.

EXAMPLE 3

Effectiveness of the Immunotherapeutic Agent as Adjuvant in the Treatment with Drugs In the infection model, female BALB/c, 129/Sv, C57BL/6 and DBA/2 mice aged between 6 to 8 weeks old and free from specific pathogen were used.

A virulent strain of *Mycobacterium tuberculosis* was cultured in Proskauer-Beck medium until a middle logarithmic phase was reached and was kept in 1-mL aliquots at −70° C. until used.

The mice were inoculated in a Middelbrook aerosol inoculation apparatus that provides approximate inoculums of 10-50 viable bacilli in the lungs.

The bacillary concentration, i.e., the number of viable bacilli, is determined by the incubation of serial dilutions of homogenized left lung and spleen in Middelbrook 7H11-type agar. Left lung and spleen samples were homogenized in the presence of 1 mL of PBS buffer.

I) Treatment with One Dose of Liposomed Immunotherapeutic Agent Simultaneously with Isoniazid Infected BALB/c type mice were divided into three groups:

Treated only with isoniazid at a dose of 25 mg/kg per day for 5 days per week for 6 weeks (Control), or Treated with isoniazid at a dose of 25 mg/kg per day for 5 days per week for 6 weeks plus an intranasal dose of 180 μg of liposomed immunotherapeutic agent, the object of the invention, or Treated with isoniazid at a dose of 25 mg/kg per day for 5 days a week for 6 weeks plus an intraperitoneal 180 μg dose of liposomed immunotherapeutic agent, the object of the invention Treatment with the antibiotic isoniazid was started at week 9 and was continued until week 15.

The dose of the liposomed immunotherapeutic agent, the object of the invention, was administered at week 13.

At week 15, the animals were killed and the bacillary concentration in the left lung and the spleen was determined.

The bacillary concentrations, established following the method described in the introduction of Section C, were significantly lower in the lungs of the vaccinated animals, whereas the results in the spleen were not statistically different compared with the Control group.

The results, expressed as UFC/mL, are shown in Table 1:

TABLE 1

| Mice group | Lung | Spleen |
|---|---|---|
| Control | 7.5 ± 2.89 | 0.75 ± 0.33 |
| Intranasal | <2 ± 0* | 0.4 ± 0.2 |
| Intraperitoneal | <2 ± 0* | 0.52 ± 0.44 |

*= statistically significant value compared to the Control group, $p < 0.05$

It may be seen that animals treated with the liposomed immunotherapeutic agent, the object of the invention, administered intranasally and intraperitoneally simultaneously with isoniazid showed a considerably lower number of bacilli in the lungs than mice treated with the antibiotic isoniazid alone.

Taking into account that the number of established bacilli includes all bacilli, both those that are in an active phase and those that are in a non-active phase, the treatment with the liposomed immunotherapeutic agent would allow to reduce the time of treatment with the antibiotic, since it considerably reduces the number of bacilli that may change with time into an active phase.

II) Treatment with Three Doses of Liposomed Immunotherapeutic Agent Following Treatment with Rifampicin and Isoniazid Infected 129/Sv-type mice were divided into two groups:
Treated with isoniazid at a dose of 25 mg/kg per day for 5 days per week for four weeks and rifampicin at a dose of 10 mg/kg per day for 5 days per week for four weeks (Control), and
Also treated with three 180 μg doses of liposomed immunotherapeutic agent, the object of the invention, administered subcutaneously following treatment with rifampicin and isoniazid The treatment with the antibiotic isoniazid was begun at week 9 and was continued for 4 weeks. At week 13, the treatment with rifampicin was started and concluded at week 17.

At weeks 17, 19 and 21, three doses of liposomed immunotherapeutic agent, the object the invention, were administered.

At week 22, the animals were killed and the bacillary concentrations in the left lung and in the spleen were established.

The bacillary concentration was significantly lower in the lungs of vaccinated animals compared with the Control group, whereas no significant differences were found in the spleen between the Control group mice and those who were also treated with the liposomed immunotherapeutic agent.

The results, expressed in $\log_{10}$ UFC/mL, are shown in Table 2:

TABLE 2

| Mice group | Lung | Spleen |
| --- | --- | --- |
| Control | 2.67 ± 0.83 | 2.35 ± 1.18 |
| Subcutaneous | 1.61 ± 0.58* | 1.37 ± 1.02 |

*= statistically significant value compared to the Control group, $p < 0.05$

It may be seen that the mice treated with the liposomed immunotherapeutic agent, the object of the invention, administered subcutaneously and after treatment with the antibiotics isoniazid and rifampicin showed a considerably lower number of bacilli in the lungs than mice treated with the antibiotics alone.

The same conclusion of Section I) may be applied in this case.

III) Treatment with Three Doses of Liposomed Immunotherapeutic Agent Simultaneously with Isoniazid Infected C57BL/6 type mice were divided into two groups:
Treated with isoniazid alone at a dose of 25 mg/kg per day for 5 days per week for 8 weeks (Control), and
Also treated with three 180 μg doses of the liposomed immunotherapeutic agent, the object of the invention, administered intranasally.

At week 9, the treatment with the antibiotic isoniazid began and was continued until week 17.

The doses of the liposomed immunotherapeutic agent were administered at weeks 13, 15 and 17.

The mice were sacrificed at weeks 15 and 28 and the bacillary concentrations in the left lung and the spleen were established.

The bacillary concentration was significantly lower in the lungs of vaccinated animals after administration of one or three doses (corresponding to weeks 15 and 28, respectively), compared to the Control group.

The results obtained for the lungs following one dose of the immunotherapeutic agent (week 15) and following 3 doses (week 28), expressed in $\log_{10}$ UFC/mL, are shown in Table 3:

TABLE 3

| Mice group | Week 15 (1 dose) | Week 28 (3 dose) |
| --- | --- | --- |
| Control | 2.34 ± 0.24 | 3.86 ± 0.41 |
| Intranasal | 1.59 ± 0.61* | 3.48 ± 0.18* |

*= statistically significant value compared to the Control group, $p < 0.05$

It may be seen that the mice treated with only one dose of the liposomed immunotherapeutic agent administered by intranasal route, simultaneously with a treatment with the antibiotic isoniazid, show a considerably lower number of bacilli in the lungs than the mice treated with the antibiotic alone.

The same conclusion of Section I) may be applied in this case.

As regards the spleen, the bacillary concentration was significantly lower in vaccinated animals following the administration of the 3 doses (corresponding to week 28), compared to the Control group.

The results obtained for the spleen, expressed in $\log_{10}$ UFC/mL, are shown in Table 4:

TABLE 4

| Mice group | Week 15 | Week 28 |
| --- | --- | --- |
| Control | 1.47 ± 0.44 | 3.84 ± 0.48 |
| Intranasal | 1.41 ± 0.58 | 3.43 ± 0.29* |

*= statistically significant value compared to the Control group, $p < 0.05$

It may be seen that the mice treated with three doses of the immunotherapeutic agent, the object of the invention, administered intranasally simultaneously with treatment with the antibiotic isoniazid showed a considerably lower number of bacilli in the lungs than mice treated with the antibiotic alone.

The same conclusion of Section I) may be applied in this case.

IV) Comparative Trial to Study the Effect of the Antibiotics, the Liposomed Immunotherapeutic Agent and the Interactions between the Two Several trials with DBA/2 mice have been conducted, following a $2^2$ factorial design under the conditions shown in Table 5:

TABLE 5

| Trial | Antibiotic | Liposomed immunotherapeutic agent |
| --- | --- | --- |
| 1 | No | No |
| 2 | Yes | No |
| 3 | No | Yes |
| 4 | Yes | Yes |

In trial 1, the infected mice were maintained without any treatment.

In trial 2, the infected mice received the antibiotic isoniazid alone at a dose of 25 mg/kg per day for 5 days per week for 4 weeks and rifampicin at a dose of 10 mg/kg per day for 5 days per week for 4 weeks, starting at week 9 after infection.

In trial 3, the infected mice were treated with three 180 μg doses of liposomed immunotherapeutic agent alone, administered subcutaneously at weeks 9, 11 and 15 after infection.

In trial 4, treatment with the antibiotic isoniazid was begun at week 9 and was administered for 4 weeks. At week 13, the treatment with rifampicin was initiated and was concluded at week 17. At weeks 17, 19 and 21, three doses of the liposomed immunotherapeutic agent, object of the invention, were administered.

At week 22, all the animals were killed and the bacillary concentrations in the left lung were established. The results obtained for the lungs are expressed in $\log_{10}$ UFC/mL and are shown in Table 6:

TABLE 6

| Trial | Antibiotic | Liposomed immunotherapeutic agent | $\log_{10}$ UFC/mL |
|---|---|---|---|
| 1 | No | No | 5.37 ± 0.27 |
| 2 | Yes | No | 3.29 ± 0.8* |
| 3 | No | Yes | 5.69 ± 0.22 |
| 4 | Yes | Yes | 0.69 ± 0** |

*= statistically significant value compared to trials 1, 3 and 4 for $p < 0.05$;
**= statistically significant value compared to trials 1, 2 and 3 for $p < 0.05$ It may be seen that the combined treatment of the antibiotics isoniazid and rifampicin with the liposomed immunotherapeutic agent, the object of the invention, causes a considerably higher reduction in the number of bacilli compared with the reduction found with any of the other two factors (antibiotics and liposomed immunotherapeutic agent) alone.

Taking into account that the number of established bacilli includes all bacilli, both those in an active phase and those in a non-active phase, the treatment with the liposomed immunotherapeutic agent in association with other drugs would allow to reduce the time of treatment with those drugs, since it considerably reduces the number of bacilli that may change with time into an active phase.

Although the invention is illustrated and described herein with reference to specific embodiments, the invention is not intended to be limited to the details shown. Rather, various modifications may be made in the details within the scope and range of equivalents of the claims and without departing from the invention.

The invention claimed is:

1. A method to obtain an immunotherapeutic agent that contains cell wall fragments from a virulent *Mycobacterium tuberculosis*-complex (MTB-C) strain of cells consisting essentially of the sequential steps of
    a) culturing the cells for a period of at least three weeks,
    b) homogenizing the cells in the presence of a non-ionic surfactant to produce a homogenate comprising non-fragmented cells, cell wall fragments, and solubilized cell compounds, wherein the non-ionic surfactant is selected from the group consisting of alkylphenol ethoxylates and ethoxylated sorbitan esters,
    c) centrifuging the homogenate to separate the cell wall fragments from the non-fragmented cells and the solubilized cell compounds,
    d) washing the cell wall fragments and further inactivating any remaining virulent cells to obtain the immunotherapeutic agent, and
    e) optionally, lyophilizing the immunotherapeutic agent;
    wherein the immunotherapeutic agent is substantially free of non-fragmented cells and solubilized cell compounds.

2. The method according to claim 1 wherein the cell culturing period ranges from 3 to 4 weeks.

3. The method according to claim 1 wherein the non-ionic surfactant is an octylphenol ethoxylate compound.

4. The method according to claim 3 wherein the non-ionic surfactant is an octylphenol ethoxylate having 7-8 mol of ethylene oxide.

5. The method according to claim 1 wherein the cells are homogenized in a buffered medium having a neutral pH.

6. The method according to claim 5 wherein the medium is buffered with PBS buffer.

7. The method according to claim 1
    wherein step e) lyophilizing the resulting immunotherapeutic agent is performed.

8. The method according to claim 7 wherein the cell culturing period ranges from 3 to 4 weeks.

9. The method according to claim 7 wherein the non-ionic surfactant is an octylphenol ethoxylate compound.

10. The method according to claim 9 wherein the non-ionic surfactant is an octylphenol ethoxylate having 7-8 mol of ethylene oxide.

11. The method according to claim 7 wherein the cells are homogenized in a buffered medium having a neutral pH.

12. The method according to claim 11 wherein the medium is buffered with PBS buffer.

13. An immunotherapeutic agent comprising cell wall fragments from a virulent *Mycobacterium tuberculosis*-complex (MTB-C) strain of cells obtained by a process consisting essentially of the steps of:
    a) culturing the cells for a period of at least three weeks,
    b) homogenizing the cells in the presence of a non-ionic surfactant to produce a homogenate comprising non-fragmented cells, cell wall fragments, and solubilized cell compounds, wherein the non-ionic surfactant is selected from the group consisting of alkylphenol ethoxylates and ethoxylated sorbitan esters,
    c) centrifuging the homogenate to separate the cell wall fragments from the non-fragmented cells and the solubilized cell compounds,
    d) washing the cell wall fragments and further inactivating any remaining virulent cells to obtain the immunotherapeutic agent, and
    e) optionally, lyophilizing the immunotherapeutic agent;
    wherein the immunotherapeutic agent is substantially free of non-fragmented cells and solubilized cell compounds.

14. The immunotherapeutic agent according to claim 13, wherein the cell culturing period ranges from 3 to 4 weeks.

15. The immunotherapeutic agent according to claim 13, wherein the non-ionic surfactant is an octylphenol ethoxylate compound.

16. The immunotherapeutic agent according to claim 15, wherein the non-ionic surfactant is an octylphenol ethoxylate having 7-8 mol of ethylene oxide.

17. The immunotherapeutic agent according to claim 13, wherein the cells are homogenized in a buffered medium having a neutral pH.

18. The immunotherapeutic agent according to claim 17, wherein the medium is buffered with PBS buffer.

19. A pharmaceutical composition comprising the immunotherapeutic agent of claim 13.

20. A pharmaceutical composition comprising the immunotherapeutic agent of claim 13, wherein the immunotherapeutic agent has been lyophilized.

21. The pharmaceutical composition according to claim 19, in the form of liposomes.

22. The pharmaceutical composition according to claim 21, wherein the liposomes comprise auxiliary lipids selected from neutral and/or negatively charged phospholipids, and sterols.

23. The pharmaceutical composition according to claim 22, wherein the phospholipids are selected from phosphatidylcholine, phosphatidylserine, and phosphatidylinositol.

24. The pharmaceutical composition according to claim 23, wherein the sterols are selected from cholesterol and biliar salts.

25. The pharmaceutical composition according to claim 24, further comprising vitamin E.

26. A method for the combined treatment of tuberculosis comprising administering the immunotherapeutic agent of claim 13 in combination with at least one drug suitable for the treatment of tuberculosis.

27. The method of claim 26 wherein the combined therapy is sequential or simultaneous.

28. The method of claim 26, wherein the drug is selected from the group consisting of isoniazid, rifampicin, and combinations thereof.

* * * * *